(12) United States Patent
Lucas et al.

(10) Patent No.: US 8,333,105 B2
(45) Date of Patent: Dec. 18, 2012

(54) PRECONCENTRATORS AND METHODS OF MAKING AND USING THE SAME

(75) Inventors: Jonathan Day Lucas, Encinitas, CA (US); Manna Leon Warburton, San Diego, CA (US); Todd Mlsna, Carlsbad, CA (US); Sanjay V. Patel, San Diego, CA (US); Stephen Terrence Hobson, San Marcos, CA (US)

(73) Assignee: Seacoast Science, Inc., Carlsbad, CA (US)

( * ) Notice: Subject to any disclaimer, the term of this patent is extended or adjusted under 35 U.S.C. 154(b) by 99 days.

(21) Appl. No.: 12/771,835

(22) Filed: Apr. 30, 2010

(65) Prior Publication Data

US 2010/0307224 A1 Dec. 9, 2010

Related U.S. Application Data

(63) Continuation of application No. 11/836,736, filed on Aug. 9, 2007, now Pat. No. 8,117,896.

(60) Provisional application No. 60/821,943, filed on Aug. 9, 2006.

(51) Int. Cl.
*G01N 30/08* (2006.01)
(52) U.S. Cl. .................................... 73/23.41
(58) Field of Classification Search ................. 73/23.41
See application file for complete search history.

(56) References Cited

U.S. PATENT DOCUMENTS

| 4,003,257 A | 1/1977 | Fletcher et al. |
| 4,759,210 A | 7/1988 | Wohltjen |
| 4,805,441 A | 2/1989 | Sides et al. |
| 5,014,541 A | 5/1991 | Sides et al. |
| 5,289,715 A | 3/1994 | Staples et al. |
| 5,447,556 A | 9/1995 | Pleil et al. |
| 5,476,794 A | 12/1995 | OBrien et al. |
| 5,551,278 A * | 9/1996 | Rounbehler et al. ........... 73/1.06 |

(Continued)

FOREIGN PATENT DOCUMENTS

| EP | 0 590 932 | 4/1994 |
| WO | WO 91/08466 | 6/1991 |

OTHER PUBLICATIONS

Phillips et al., "Multiplex Gas Chromatography by Thermal Modulation of a Fused Silica Capillary Column", Anal. Chem, 57, 1985, pp. 2779-2787.
Phillips et al., "Thermal Modulation for Sample Introduction into Ultra-Small Diameter Capillary Columns in GC", Int. Symp. Capil. Chrom., 11, 1990, pp. 474-482.

*Primary Examiner* — Daniel Larkin
(74) *Attorney, Agent, or Firm* — Arent Fox LLP

(57) ABSTRACT

Apparatus, systems and methods are described for preconcentrators, chemical sensing systems and gas chromatographs. A preconcentrator is described that comprises a hollow enclosure containing a sorbent material. The enclosure may be a capillary tube that can be formed in to a desired shape and that may be heated. Heating may be accomplished by passing an electrical current through the capillary or other hollow enclosure form. The sorbent material can be a liquid, a solid, a porous ceramic material and/or a chemiselective polymer. The sorbent material can be coated to the inner wall of the enclosure. The hollow enclosure may be maintained in an insulated chamber. The preconcentrator acts to concentrate a vapor passed through the preconcentrator to a chemical sensing array that can detect chemicals present in the vapor. A gas passed through the hollow enclosure can provide a chemically concentrated input to a chromatographic column.

11 Claims, 14 Drawing Sheets
(10 of 14 Drawing Sheet(s) Filed in Color)

U.S. PATENT DOCUMENTS

| | | |
|---|---|---|
| 5,795,368 A | 8/1998 | Wright et al. |
| 6,223,584 B1 | 5/2001 | Mustacich et al. |
| 6,902,701 B1 | 6/2005 | Hughes et al. |
| 7,314,505 B1 | 1/2008 | Wheeler et al. |
| 8,117,896 B2 * | 2/2012 | Lucas et al. |
| 2006/0191414 A1 | 8/2006 | Lange et al. |

* cited by examiner (a) 7 ketones mixture: separated and detected using a Mini GC.

(b) One set of ketones expanded (c) Ketone sensor and water sensor aligned indicating that the shoulder on the Hexanone sensor signal is due to the presence of water.

PRECONCENTRATORS AND METHODS OF MAKING AND USING THE SAME

CROSS-REFERENCE TO RELATED APPLICATIONS

This application is a continuation of U.S. patent application Ser. No. 11/836,736, entitled "Preconcentrators And Methods Of Making And Using The Same" filed Aug. 9, 2007, which claims priority to U.S. Provisional Application No. 60/821,943, filed Aug. 9, 2006 and entitled "Preconcentrators And Methods Of Making And Using The Same" which applications are incorporated herein by reference for all purposes.

BACKGROUND OF THE INVENTION

1. Field of the Invention

The present invention relates generally to chemical sensing methods and more particularly to chemical sensing methods employing preconcentrators and chromatography columns and more particularly to chemical sensing methods used in portable systems.

2. Description of Related Art

Conventional systems used for the identification of volatile chemicals whether alone or as part of complex mixtures present in trace amounts to high concentrations tend to heavily consume power and are typically bulky and non-portable. Examples of volatile chemicals include chemical warfare agents and explosives and conventional systems are typically used to monitor locations where such chemicals are used, produced or stored. Portable chemical sensing systems typically require the use of compressed gases, thereby limiting their utility.

Frequently used chemical analysis tools consist of gas chromatographs ("GC") typically provided with a flame ionization detector ("FID") and thermal conductivity detectors ("TCD"). Mass spectrometers ("MS") are also used in chemical analysis. Conventionally, these tools are confined to bench top instruments that require a trained operator to transfer vapor or liquid samples to a laboratory for testing. Detectors such as the FID and TCD require a carrier gas to detect the target chemicals tethering the instrument to a gas cylinder and, consequently, usually to a laboratory. For example, the NIOSH method for naphthalene detection uses a GC with FID in which helium is used as a carrier gas.

Some conventional tubular preconcentrators have been used but are generally formed from relatively large one eighth inch (or larger) inside diameter metal tubing 1 stuffed with glass fibers coated in some absorptive material. The tubing 1 is typically wrapped in nichrome wire 3 which heats the tubing when an electrical current is passed through it as shown in FIG. 1a. Such preconcentrators suffer from deficiencies that include the escape of heat from the nichrome wire 3 to the surroundings, the requirement of heating a relatively large thermal mass of the tubing 1 in order to facilitate heat transfer to the inside of the metal tube 1 (causing power drain and time lags) and the hinderance of heat flow at the interior of the tube 2 because of the poor heat conduction pathways of glass fiber matrices, which also hamper the passage of the carrier gas. These deficiencies impede uniform heating of the interior matrix to ensure uniform desorption of target chemicals.

BRIEF SUMMARY OF THE INVENTION

Certain embodiments of the invention provide systems, methods and apparatus useful in chemical sensing. A preconcentrator comprises a hollow enclosure containing a sorbent material wherein the hollow enclosure may be heated. Heating can be accomplished by passing an electrical current through resistive walls of the hollow enclosure. In certain embodiments the enclosure comprises an electrically conductive or semiconductive material that can be a metal. In some embodiments the metal is stainless steel. In certain embodiments the enclosure comprises a sorbent material that may be in solid and/or liquid states. In some embodiments the sorbent material comprises a porous ceramic material and/or a chemiselective polymer. In certain embodiments the sorbent material is coated to the inner wall of the enclosure. In certain embodiments the enclosure is configured to be heated or cooled.

In certain embodiments the hollow enclosure may be provided in a compact configuration such as a helical coil. In certain embodiments the hollow enclosure may be maintained within an insulated chamber using a vacuum and/or an insulating material. In some embodiments the insulating material can be Styrofoam.

Certain embodiments provide sensing systems that can comprise a preconcentrator and a chemical sensing device. The sensing systems may include gas chromatographs and can comprise temperature and flow sensors and controllers.

Certain embodiments employ methods that comprise passing a gas or vapor over a sorbent material within a hollow enclosure, heating the hollow enclosure to release concentrations of selected chemicals absorbed by the sorbent materials and sensing the presence and quantity of the selected chemicals in an outflow of the hollow enclosure.

Certain embodiments of the invention comprise preconcentrators and chemical sensor systems including portable preconcentrators and chemical sensor systems. Sorption and desorption can be controlled using thermal cycling of a capillary tube preconcentrator coated with a sorbent material. A system according to certain aspects of the invention can be controlled by one or more control systems that may comprise an electronic control circuit board and associated software that can maintain flow of test and support materials and can regulate thermal cycling of the preconcentrator. Typically, the system requires no valves. Consequently, a chemical sensing and detection system can be provided in a package having a small form factor and the system may be lightweight, and have low power requirements.

In certain embodiments, a preconcentrator may be included in a chemical sensing system. The preconcentrator can concentrate target vapors by several orders of magnitude over ambient concentrations and therefore can improve the performance and operability of the chemical sensing system.

In certain embodiments, a chemical preconcentrator may employ certain materials having properties which allow the materials to absorb and/or adsorb target materials in a variety of different physical states. For example, a gas may be absorbed or adsorbed onto a solid or liquid. In another example, a liquid may be absorbed or adsorbed onto a solid material. As described in further detail below, various sorbent materials for trapping target chemicals may be used in chemical preconcentrators. These sorbent may include customized materials, commercial materials or licensed materials provided, for example, by organizations including private or governmental entities. Materials used in sensing applications may be designed with high temperature stability facilitating repeated thermal cycling. Materials used in sensing applications may be specifically tailored for sorption of certain chemicals or classes of chemicals.

In certain embodiments, gas chromatography may be used for chemical sensing and detection. Aspects of the present invention can enable the use of techniques similar in concept to a gas chromatograph but which perform with improved selectivity. For example, high vapor pressure chemicals may be caused to pass through the system quickly, while lower vapor pressure chemicals can be retained in the preconcentrator until the temperature is increased to the point where the lower vapor pressure chemicals these compounds are eluted or desorbed. Lower vapor pressure chemicals may include pesticides, explosives, nerve agents, and various toxic industrial chemicals.

Certain chemicals retained or absorbed by the preconcentrator due to their low vapor pressure nature, or by specific interactions with the support polymer inside the preconcentrator will typically desorb from the preconcentrator and be detected by a sensor upon increasing temperature to a desired level. Furthermore, an increased collection time may be directly correlated to increased sensor response. In other words, higher sensitivities may be achieved by simply collecting target vapors for a longer time in the preconcentrator.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
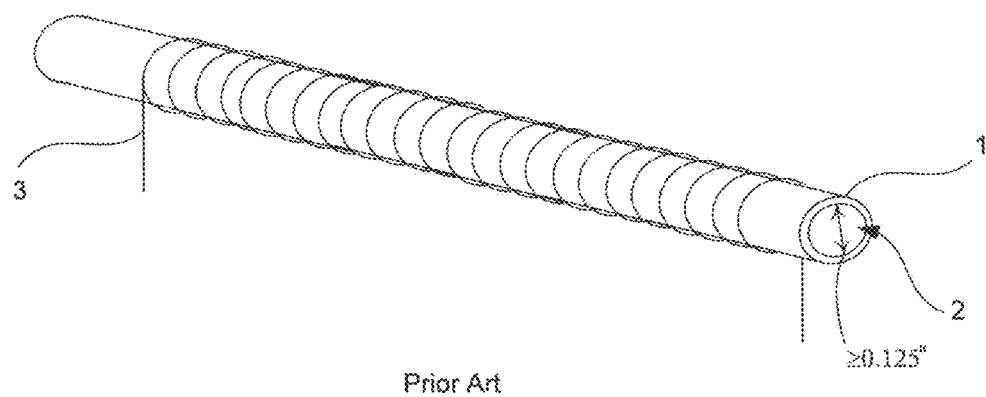
FIG. 1a depicts a prior art preconcentrator.

Embodiments of the present invention will now be described in detail with reference to the drawings, which are provided as illustrative examples so as to enable those skilled in the art to practice the invention. Notably, the figures and examples below are not meant to limit the scope of the present invention to a single embodiment, but other embodiments are possible by way of interchange of some or all of the described or illustrated elements.

For purposes of this description, the term adsorption refers to a process where a target chemical or compound is accumulated on the surface of an adsorbing material and absorption refers to a process where a target chemical or compound is taken up within the volume of the absorbing material rather than on the surface of the material. For purposes of this description, desorption refers to a converse process in which a target is released from a material. For purposes of this description, sorbent material refers to material that has absorptive properties, adsorptive properties or a combination of absorptive and absorptive properties. For purposes of this description, sorption refers to the processes of absorption or adsorption and desorption refers to a converse process.

Preconcentration

Certain embodiments of the invention comprise preconcentrators and chemical sensor systems including portable preconcentrators and chemical sensor systems. Sorption and desorption can be controlled using thermal cycling of a capillary tube preconcentrator coated with a sorbent material. A system according to certain aspects of the invention can be controlled by one or more control systems that may comprise an electronic control circuit board and associated software that can maintain flow of test and support materials and can regulate thermal cycling of the preconcentrator. Typically, the system requires no valves. Consequently, a chemical sensing and detection system can be provided in a package having a small form factor and the system may be lightweight, and have low power requirements.

In certain embodiments, a preconcentrator may be included in a chemical sensing system. The preconcentrator can concentrate target vapors by several orders of magnitude over ambient concentrations and therefore can improve the performance and operability of the chemical sensing system.

In certain embodiments, a chemical preconcentrator may employ certain materials having properties which allow the materials to absorb and/or adsorb target materials in a variety of different physical states. For example, a gas may be absorbed or adsorbed onto a solid or liquid. In another example, a liquid may be absorbed or adsorbed onto a solid material. As described in further detail below, various sorbent materials for trapping target chemicals may be used in chemical preconcentrators. These sorbent may include customized materials, commercial materials or licensed materials provided, for example, by organizations including private or governmental entities. Materials used in sensing applications may be designed with high temperature stability facilitating repeated thermal cycling. Materials used in sensing applications may be specifically tailored for sorption of certain chemicals or classes of chemicals.

In certain embodiments, gas chromatography may be used for chemical sensing and detection. Aspects of the present invention can enable the use of techniques similar in concept to a gas chromatograph but which perform with improved selectivity in comparison to conventional gas chromatography methods. For example, high vapor pressure chemicals may be caused to pass through the system quickly, while lower vapor pressure chemicals can be retained in the preconcentrator until the temperature is increased to the point where the lower vapor pressure chemicals these compounds are eluted or desorbed. Lower vapor pressure chemicals may include pesticides, explosives, nerve agents, and various toxic industrial chemicals.

Certain chemicals retained or absorbed by the preconcentrator due to their low vapor pressure nature, or by specific interactions with the support polymer inside the preconcentrator will typically desorb from the preconcentrator and be detected by a sensor upon increasing temperature to a desired level. Furthermore, an increased collection time may be directly correlated to increased sensor response. In other words, higher sensitivities may be achieved by simply collecting target vapors for a longer time in the preconcentrator.

Figure 1B:
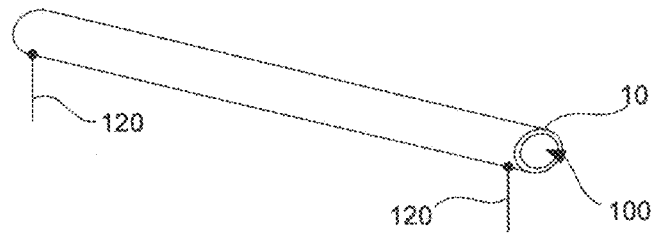
FIGS. 1b and 1c depict examples of a tube type preconcentrator according to aspects of the present invention.
Figure 1C:
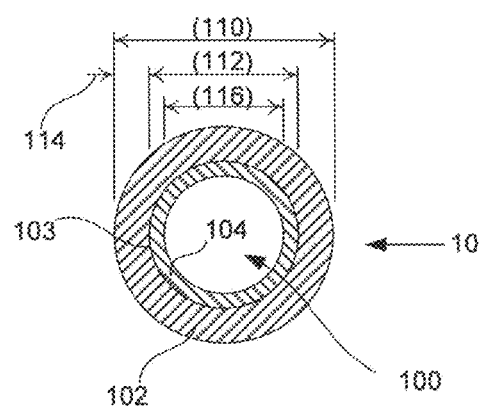

Referring now to FIGS. 1b-1c in certain embodiments of the invention a preconcentrator comprises a hollow enclosure 10 having a passage 100 through which gas or fluids can be passed. The hollow enclosure 10 may be formed as a substantially tubular structure and, for example, may be formed as a capillary tube. In the example depicted in FIGS. 1b-1c, a small diameter capillary tube 10 with an inside diameter 112 of approximately 0.025 inches can be used. The capillary tube 10 can be fabricated from a variety of materials including electrically conductive or semi-conductive materials including, for example, metals, alloys, ceramics, plastics or other materials. In certain embodiments, a capillary tube may be fabricated using a metal, such as stainless steel.

In certain embodiments, internal surfaces 103 of the hollow enclosure 10 can be coated with a sensing layer 104. The sensing layer 104 may include a sorbent material deposited or otherwise positioned inside the hollow enclosure 10 in order to facilitate collection of vapors or components of a vapor that pass through the hollow enclosure 10. For example, the inside of a capillary tube 10 may be coated with a chemiselective polymer to provide sensing layer 104.

Figure 2A:
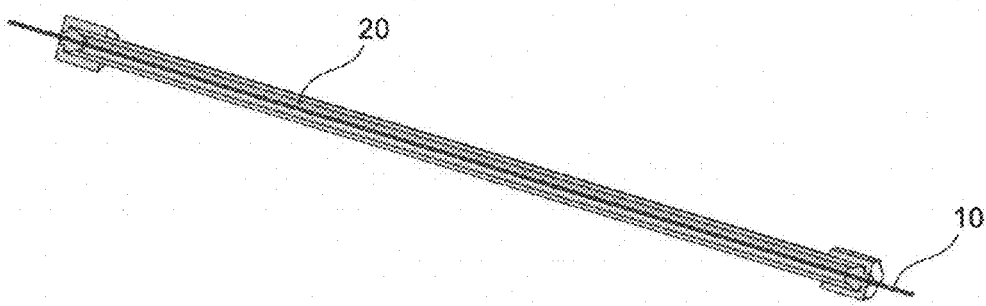
FIGS. 2a and 2b depict an example of a preconcentrator insulated by a vacuum tube.
Figure 2B:
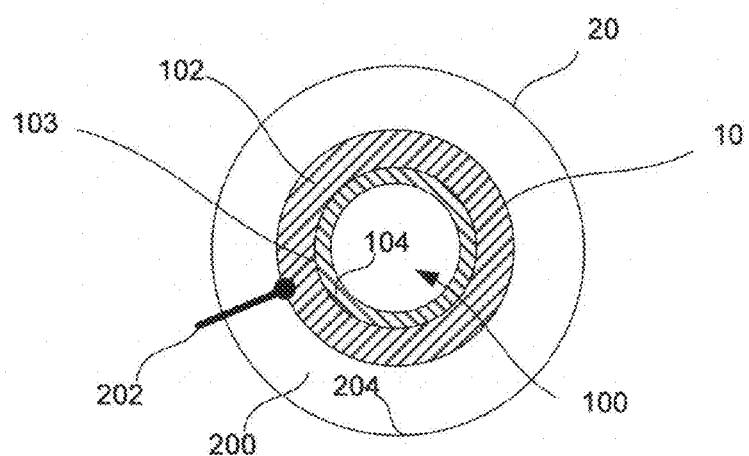

Referring additionally to FIGS. 2a and 2b, certain embodiments comprise a hollow enclosure 10 at least partially enclosed within an insulated chamber 20. The temperature of the interior 200 of the insulated chamber 20 can be monitored using a suitable temperature sensor 202 such as a thermocouple, a resistance temperature detector ("RTD") or other temperature measurement device. The temperature of the interior passage 100 of the hollow enclosure 10 may be controlled by heating or cooling the hollow enclosure 10. Heating and cooling may be effected using various techniques including electrical resistive heating, sonic heating, thermal conduction, or by any other suitable means. In one example, an electrical current can be provided directly to a hollow enclosure 10 to generate resistive heating in the tubing. In certain embodiments, heating can also be accomplished by augmenting hollow enclosure with a heating element, which can be formed using any suitable technique wrapping and or bonding a conducting or semi-conducting material around the hollow enclosure 10, by depositing conducting or semi-conducting material to the hollow enclosure 10 and/or by etching a conductive or semi-conductive trace pattern on the hollow enclosure 10. In the example of FIG. 1b, an electrical voltage can be directly applied to selected contact points 120 on the hollow enclosure 10 to generate resistive heating in the tubing; as illustrated, the hollow enclosure 10 may be a conducting or semi-conducting capillary tube. Electrically heating a capillary tube 10 maintained within an insulated chamber 20 can minimize power consumption by allowing less heat to escape during the heating process, thereby reducing power requirements even with the high surface area to volume ratio associated with certain capillary tubes 10.

Furthermore, electrically heating a conducting or semi-conducting capillary tube 10 can provide a small thermal mass, of the same order of magnitude as the thermal mass of a nichrome wire. In one example, a capillary tube 10 can be employed that has an outside diameter 110 of 0.028 inches or less and a wall thickness 114 of 0.005 inches or less. Such capillary tube 10 will typically require a relatively low power input to attain a given temperature and may exhibit a rapid response time. In certain embodiments a chemiselective polymer or other sorbent material may be coated directly onto the inner surface of the heating element so that the heating process may be fast and uniform throughout the preconcentrator.

In certain embodiments, an insulating material may be provided in the interior 200 of the insulated chamber 20 to limit thermal losses due to convection, conduction, and radiation. A variety of insulation materials can be used. In some embodiments a vacuum may be used in place of, or to supplement the actions of an insulating material. A capillary tube 10 may be suspended with an insulating enclosure 20 that has a high vacuum. The insulating enclosure 20 may be formed as a tube, temperature chamber or in any form dictated by the desired function of the preconcentrator. The use of vacuum can limit losses due to conduction and convection and in some embodiments a capillary 10 and an inner surface 204 of the insulation chamber 20 may be polished to limit losses due to radiation. In some embodiments insulation materials such as Styrofoam, fiberglass, and ceramic may be used to surround the hollow enclosure 10.

Figure 3:
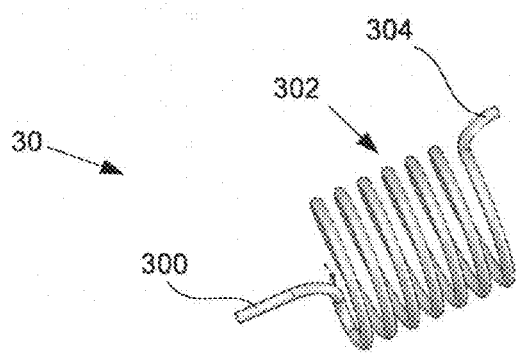
FIG. 3 depicts an example of a coiled preconcentrator tube.

In some embodiments the form factor of a preconcentrator 30 can be compressed in order to minimize length or volume of an instrument (for example). In that regard, a preconcentrator 30 may comprise a coiled capillary tube 302 as depicted in the example of FIG. 3. Several advantages may accrue from such configuration 30, including a reduction of heat loss due to reduced size packaging and lowered exposure to environmental temperature and temperature variations. In the configuration depicted, a capillary 302 with a large linear length can be maintained in a relatively small package with good insulative properties. Various methods of coiling may be employed and, in the example of a stainless steel tube capillary 302, coiling can be achieved by wrapping the stainless steel tubing around a screw shaped mandrel having grooves cut therein, the groves having a desired pitch and diameter and forming ends 300 and 304 to couple with pumps, sensors and other components of an instrument or device.

Figure 4:
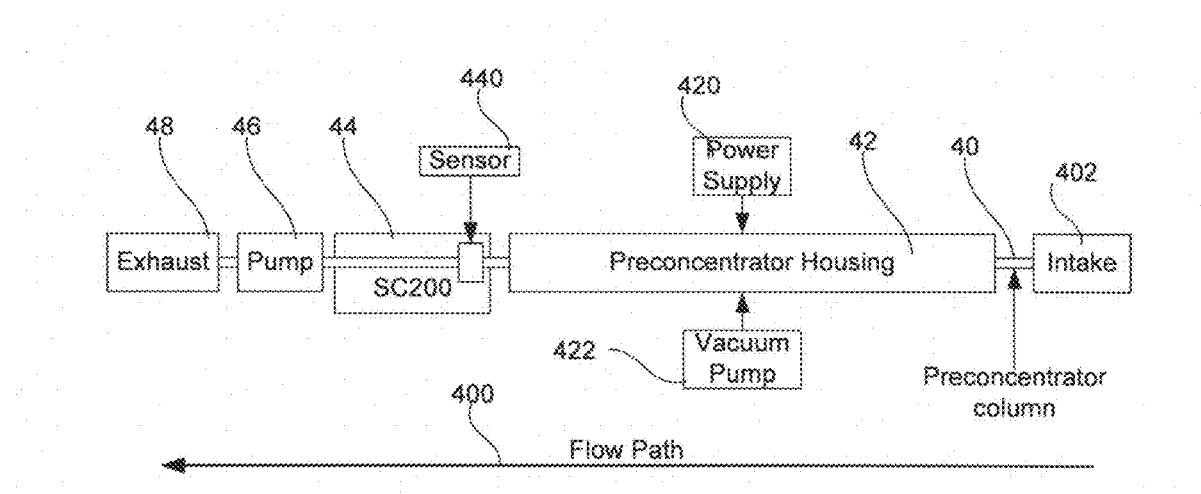
FIG. 4 is a block schematic of an example of a preconcentrator with integrated sensor.

With reference to FIG. 4, certain embodiments of the invention comprise a preconcentrator 40 integrated with one or more chemical sensors 440 to produce a chemical sensing and detection system. The chemical detector system may be small, lightweight, exhibit low power requirements and may be embodied in a portable and/or handheld chemical detector system.

In certain embodiments a flow control system may be employed to maximize sorption onto and desorption from the column. For the purposes of detecting low concentrations of a target chemical the sampling of large volumes of gas is generally anticipated, requiring the provision of high flows through the preconcentrator during the sorption cycle necessary. However, low flow may magnify sensor 440 response when a column 40 is heated and the desorption cycle has begun, allowing for lower thresholds of detection. Flow can be controlled by pumps 46, valves (not shown), or other available means of controlling gas or fluid flow.

In the illustrated example, an intake 402 can receive vapors from a target. Vapors may be received from sealed test containers or may be extracted from the environment. Intake 402 may be provided as an active or passive mechanism. Vapors received at the intake 402 are typically drawn through a preconcentrator column 40 to an exhaust 48 in a direction of flow generally indicated at 400. The preconcentrator column 40 may be housed within an insulating chamber 42 as described previously. In certain embodiments, a vacuum may be maintained within insulating chamber 42 using a pump 422. Power supply 420 may provide power for vacuum pump 422 and may supply electrical current used to heat the preconcentrator column 40. One or more sensors 440 are typically located to receive targeted components of the vapor and may be integrated with or coupled to a system controller 44 that monitors and controls operation of the device and vapor flow. For example, a computer based controller 44 may cooperate with various electronics subsystems and flow control systems to control operation of flow and flow paths as well as other functions and parameters in a chemical sensing system.

Figure 5:
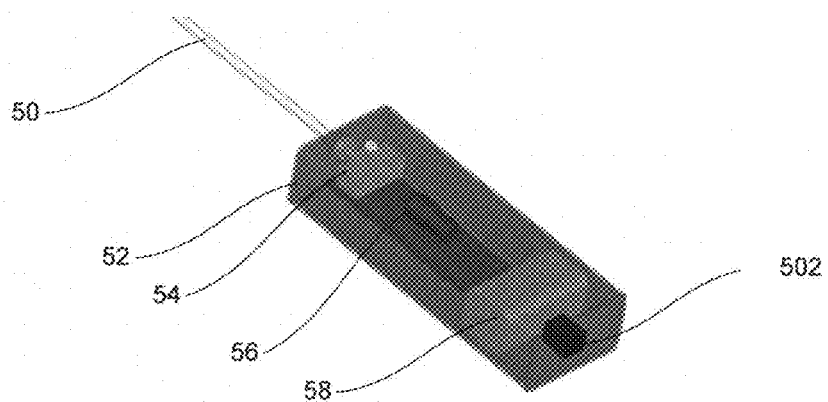
FIG. 5 illustrates packaging of the preconcentrator and sensor of FIG. 4.

FIG. 5 provides an illustration of preconcentrator 50, a sensor array 54 and associated control system 56 provided in a compact package 52. The system can be battery-powered using, for example, four AA type batteries 58 and can be thermally cycled at periodic intervals by control logic 56. Intervals are typically determined by the specific application and can be measured in seconds minutes or hours.

Figure 13:
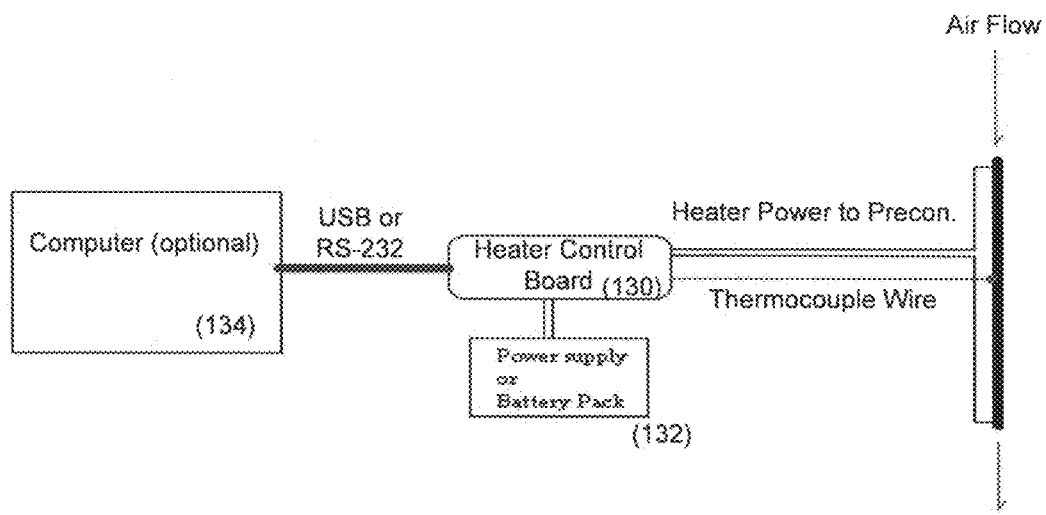
FIG. 13 depicts one example of a control system.

With reference also to FIG. 13, certain embodiments comprise a chemical detection system control system that may be employed to control operation of sensor functions such as timing, heating and cooling, flow rates, volumes, temperature sensing, or other relevant parameters. A control system may utilize miniaturized circuits to promote portability of the sensing system by minimizing component weight and power consumption. Typically, an external processor 134 communicates with one or more controllers including, for example, a heater control board 130. The external processor 134 may comprise a personal computer, a laptop computer, a PDA, one or more instruments or network of instruments, a custom processing device and any other suitable computing device such as mobile wireless devices, etc. The external processor 134 may monitor operational parameters and control a plurality of functions including heating, air/fluid flow, temperature sensing, measurement cycling, power consumption, and so on. In some embodiments, the controller 130 may be provided using one or more components that includes microprocessors, programmable logic devices, custom electronics circuits, application specific integrated circuits, software and firmware. Typically, the controller receives power from a battery or independent power supply 132 and may receive power from the external processor 134 through, for example, a USB interface.

Sorbent Coating Materials

In certain embodiments preconcentrators may be coated with a sorbent material. The sorbent material may be selected for certain applications based on properties exhibited by the sorbent material. Properties may include one or a combination of a desired thermal stability enabling the material to withstand thermal cycling, an ability to absorb one or more selected target chemicals at a first temperature (e.g. ambient temperature) and completely desorb a target chemical at a second temperature. For example, a sorbent material may be selected because it exhibits desirable absorption properties for a target chemical at ambient temperature and desorption at an elevated temperature.

Figure 6:
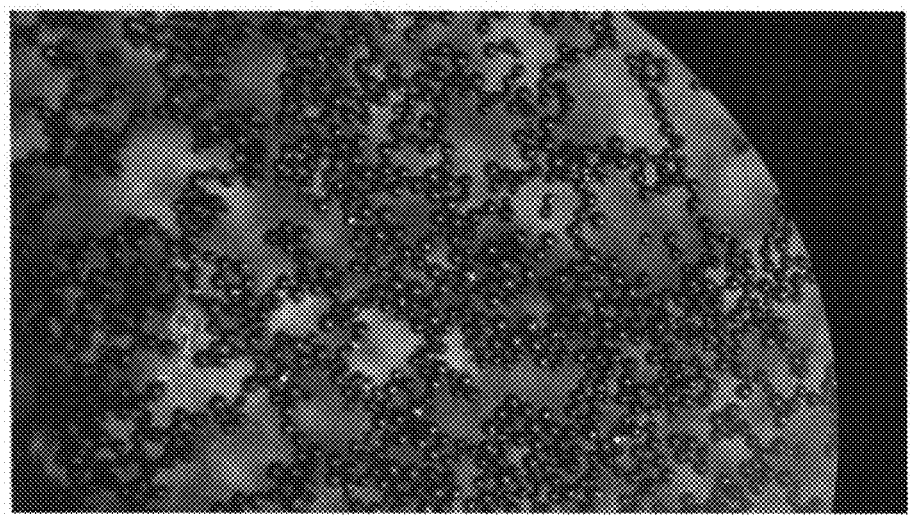
FIG. 6 shows a slurry used to coat a preconcentrator surface.
Figure 8:
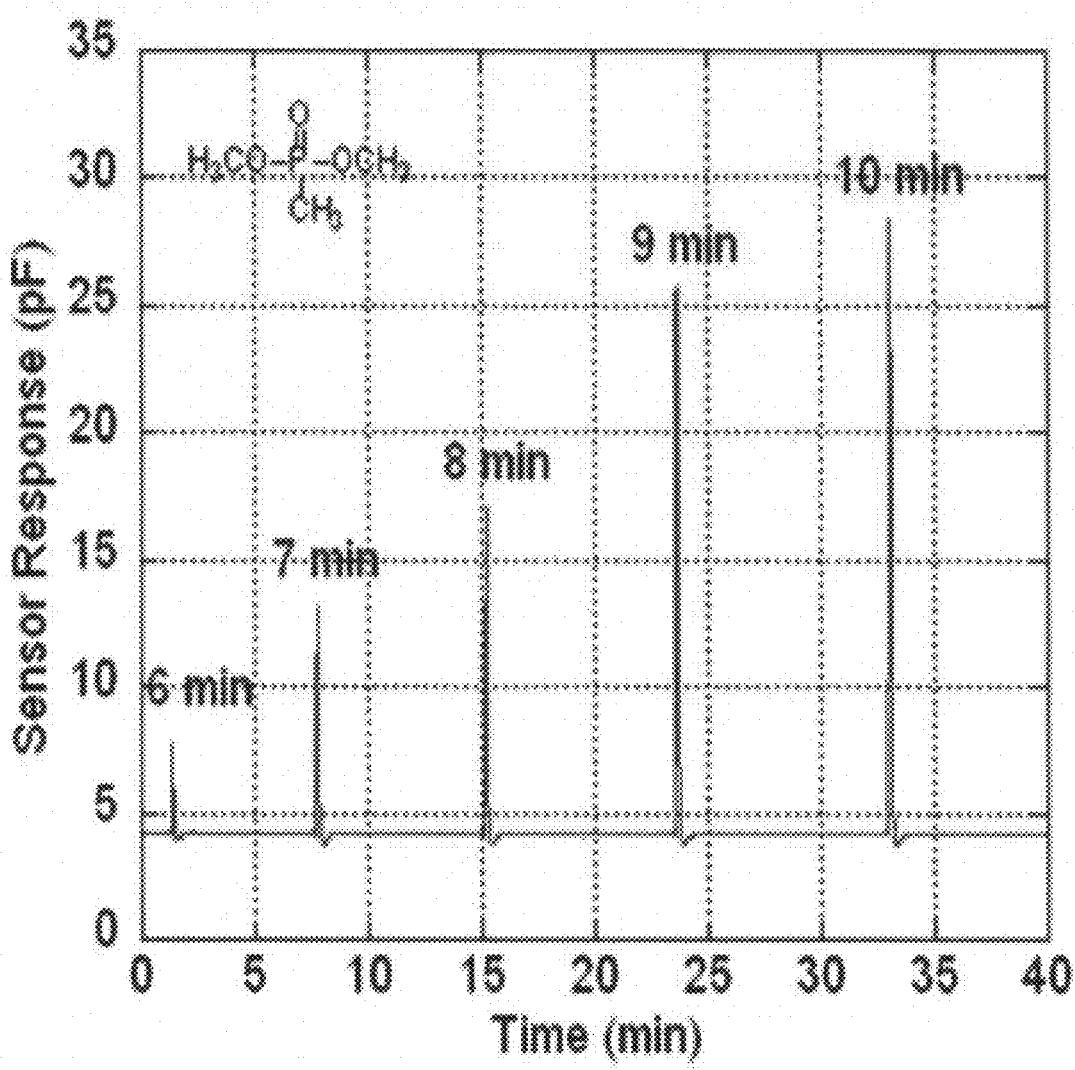
FIG. 8 is a graph showing sensor response to 5% DMMP.

In certain embodiments, a sorbent material can be physically or chemically coated onto the walls of the hollow enclosure using any suitable coating technique. In one example, coating may be accomplished by passing, drawing, pushing or forcing under pressure, concentrated volumes of viscous liquid polymers through the column followed by dry air and then heat curing at high temperature that may be, e.g., around 200° C. Viscous liquid polymers can be provided in a solvent for coating. In another example, a coating technique includes coating a commercial solid support with an absorbent polymer; examples of a commercial solid support include Poropak P, Poropak T, Tenax and Carbosieve. For example, and with reference to FIG. 8, a slurry can be formed that comprises Supelco® Carbosieve™ Mesh 80/100 or 177 to 149 µm, a customized fluoroalcohol polymer provided by Seacoast Science of Carlsbad, Calif. and a chloroform solvent. This slurry can then be coated on the inside of a preconcentration capillary tube. An example of such slurry is shown in FIG. 6.

In certain embodiments, a sorbent material may be placed within the hollow enclosure and retained or attached within the hollow enclosure using means suitable for the material type and sufficient to allow a sufficient rate of fluid/gas to flow through the hollow enclosure. In that regard, the sorbent materials may be embodied in various states and forms including, for example, a viscous liquid, a solid, a porous ceramic material and so on.

Sensing Performance

Figure 7:
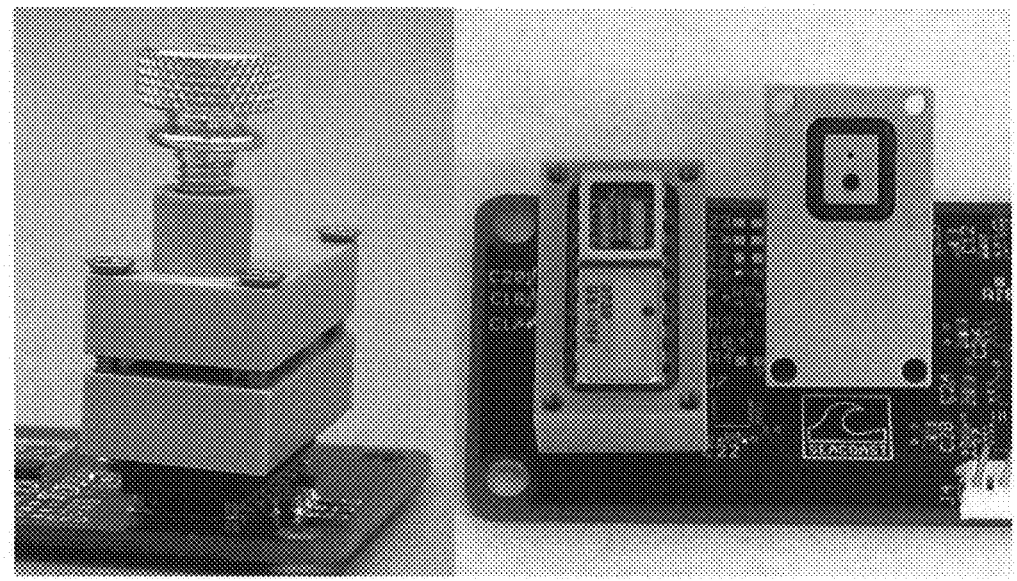
FIG. 7 shows a sensor chamber.

Improvements in sensing performance can be appreciated by considering the operation of examples of preconcentrators such as those described above and shown in FIG. 7. In one example of a testing procedure, a 5% mix of Dimethyl methyl phosphonate ("DMMP") vapor and dry air can be delivered to the preconcentrator in a flow stream. For the duration of one or more collection cycles, samples of the 5% DMMP vapor may be collected. In the example, the vapor can be collected at approximately 100 ml/m over increasing periods of time. During each of one or more detection cycles flow was reduced to 10 ml/m for twenty seconds while the preconcentrator column was heated. Results of the preconcentrator and sensor response in this example are provided in FIG. 8.

Figure 9:
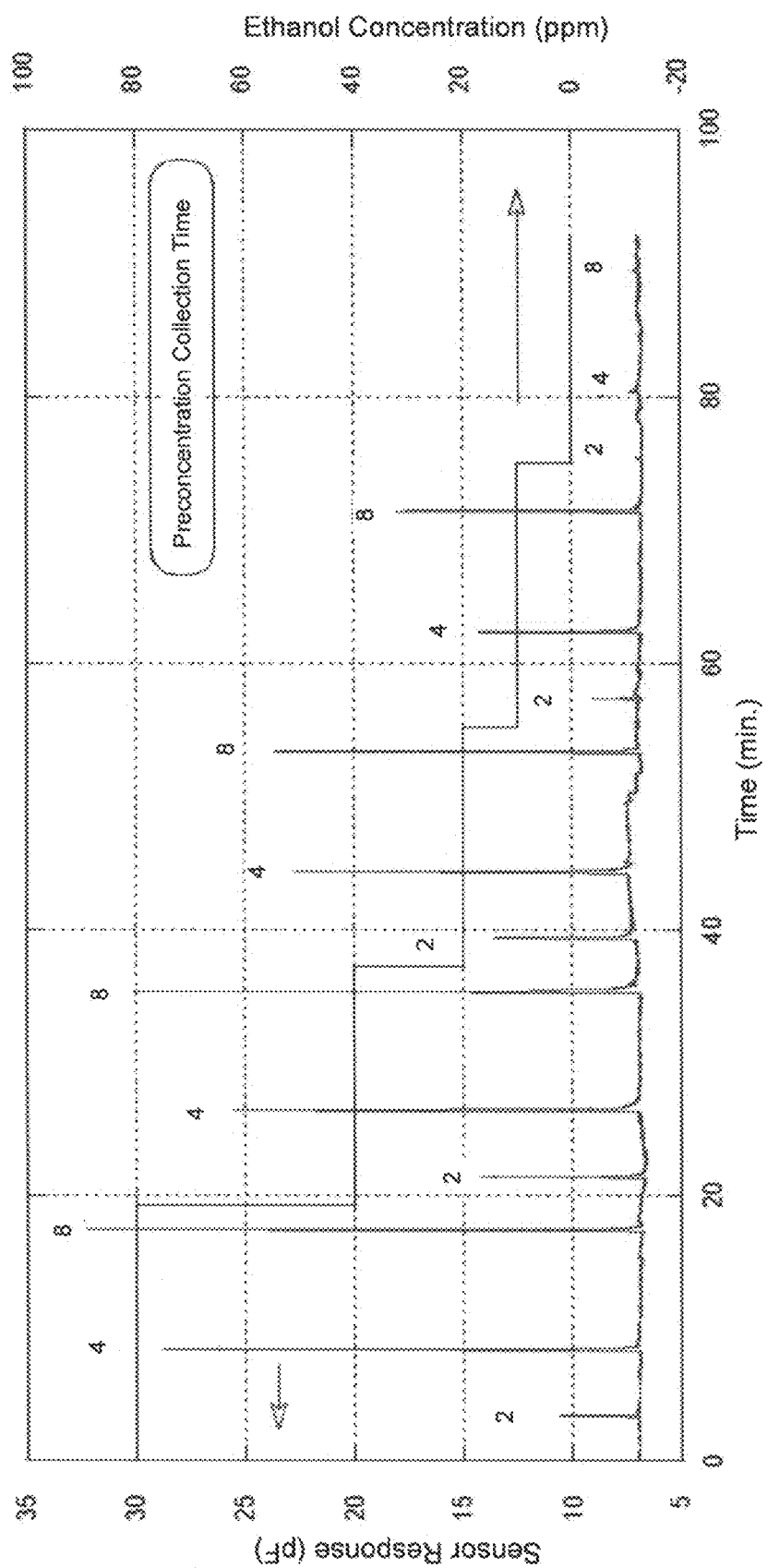
FIG. 9 is a graph related to the preconcentration of ethanol.
Figure 10:
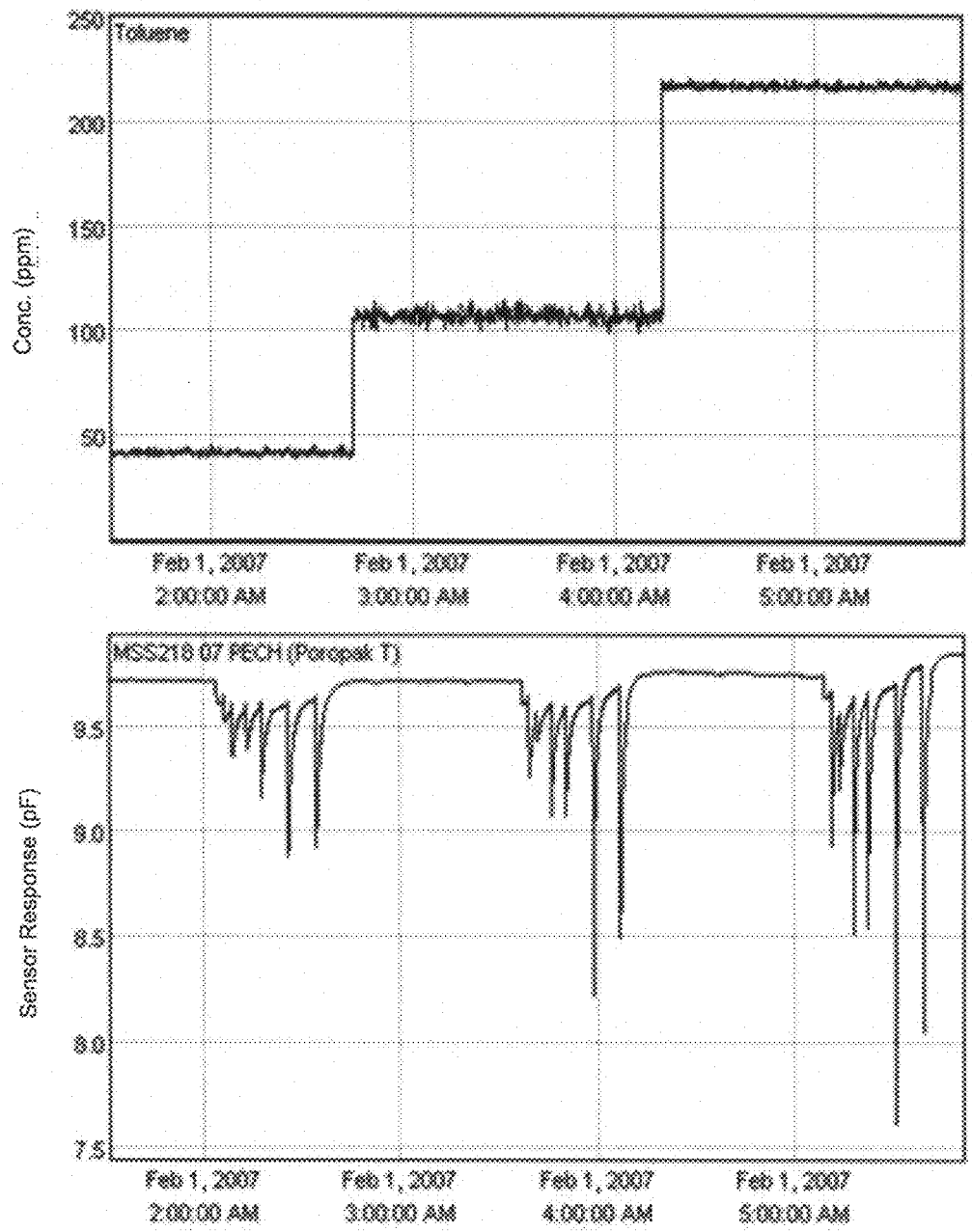
FIG. 10 depicts graphs showing results of exposing toluene to a sensor.

FIGS. 9 and 10 provide further examples of test results related to the concentration of common solvents using from a preconcentration system constructed in accordance with certain aspects of the invention. FIG. 10 depicts expanded results obtained from toluene exposures to a PECH coated sensor using a preconcentrator with Poropak T (Note that as the concentration of the chemical and collection time increase so does the sensor response). The results include examples of:

Preconcentration of 2, 4 and 8 minutes of ethanol at 80, 40, 20 and 10 ppm (FIG. 9).

Preconcentration of 2, 2, 4, 4, 8, 8 minutes of toluene at 48, 100 and 120 ppm (FIG. 10).

The results illustrate certain benefits and advantages including the increased sensor response resulting from longer collection intervals, the lowering of detection limits by almost three orders of magnitude and, in one specific example, an estimated limit of detection for ethanol of approximately 50 ppb. Furthermore, the results demonstrate a positive response to ethanol and a negative response to toluene.

Chemical sensing according to certain aspects of the instant invention may provide benefit when applied to a wide variety of targets and it is contemplated that a wide variety of other chemical targets may be susceptible to sensing using the systems and methods described herein.

Power Consumption

Figure 11:
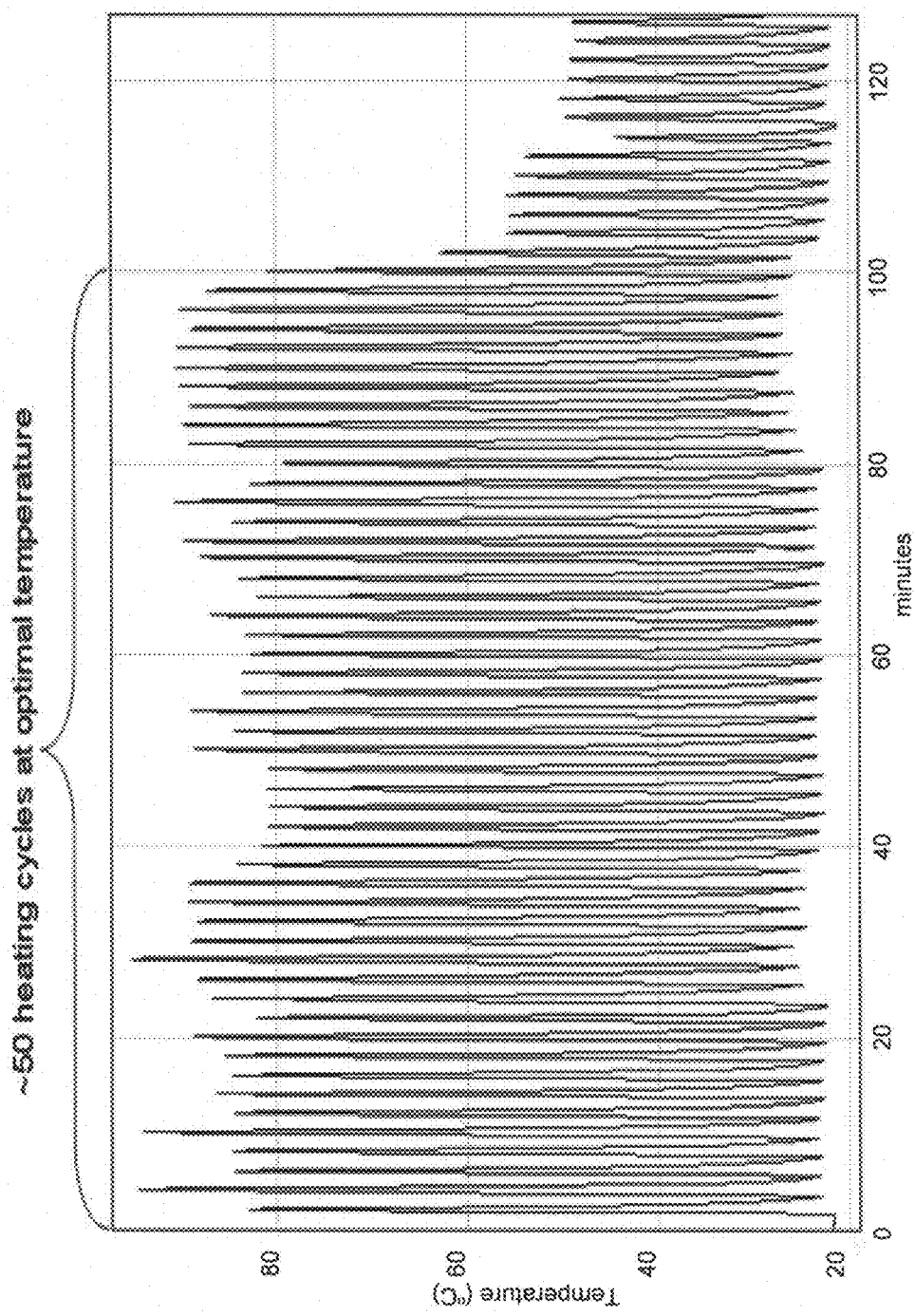
FIG. 11 depicts heating cycles of a preconcentrator.

Certain embodiments provide efficient operational performance that permits the provision of handheld and portable sensor/preconcentrator configurations. FIG. 11 illustrates the heating cycles in one example of such an embodiment. In the example, four rechargeable AA batteries can support at least fifty preconcentration cycles, corresponding to more than six detection events per hour over an eight hour day.

Figure 12:
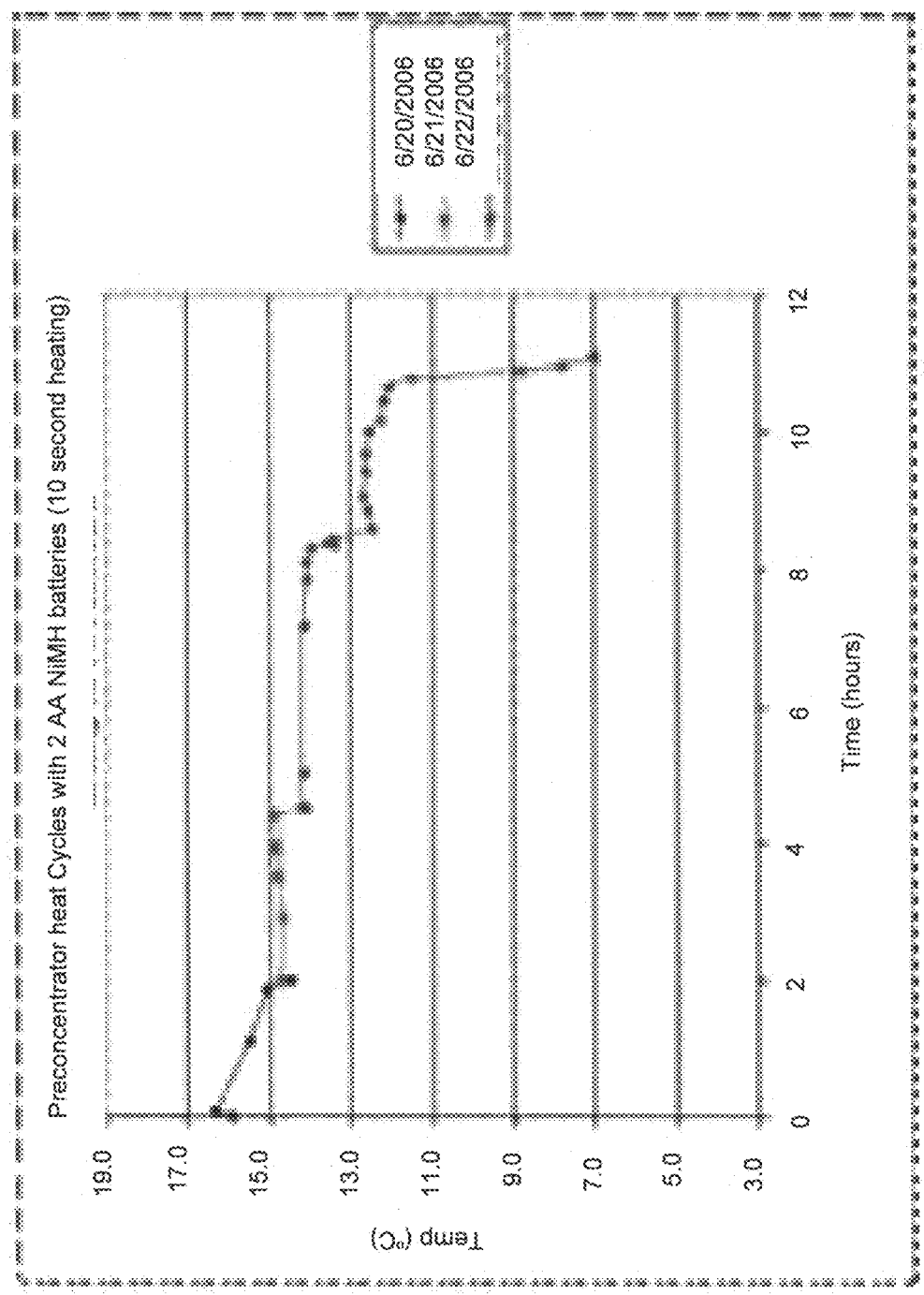
FIG. 12 depicts a graph showing open loop temperatures during heating of a preconcentrator.

FIG. 12 depicts a graph that displays an example of open loop temperature attained using two AA NiMH batteries to heat a seven inch coiled capillary pre-concentrator made of 0.028" outside diameter stainless tubing. In the example, the coiled capillary is encased in polystyrene for insulation. In the example, power from batteries was supplied for ten seconds at 140 second intervals and the coiled capillary cooled to 30-35 degrees Celsius prior to re-heating. In the example, the target temperature was set at 130-140 degrees Celsius and the test period extended over approximately eleven hours. Each cycle included a two minute collection (sorption period) and ten seconds of heating.

In certain embodiments, power can be conserved during sorption periods where only a pumping system need be operated continuously. In certain embodiments, a feedback controlled pulse width modulated power supply can be employed to extend battery life.

Preconcentration with Chromatography

Figure 14:
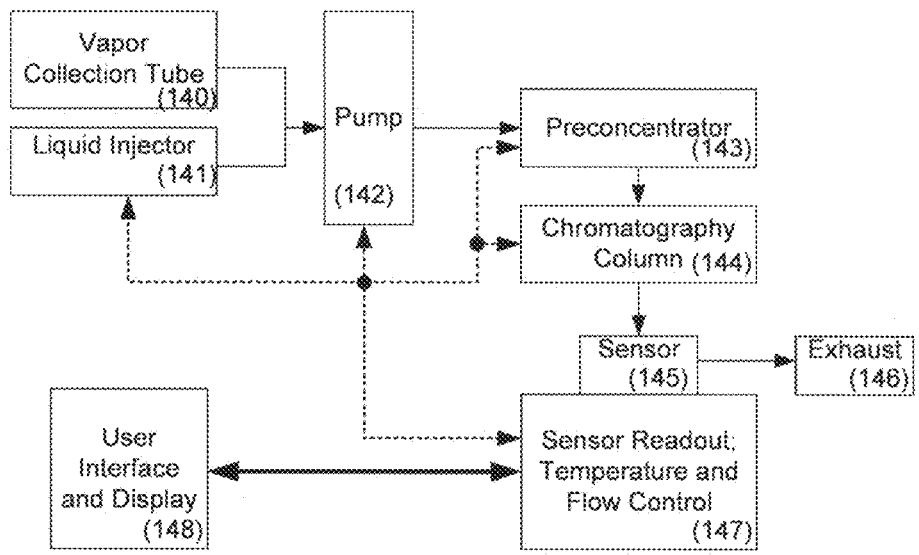
FIG. 14 is a block schematic of a simplified example of a mini-GC.
Figure 15:
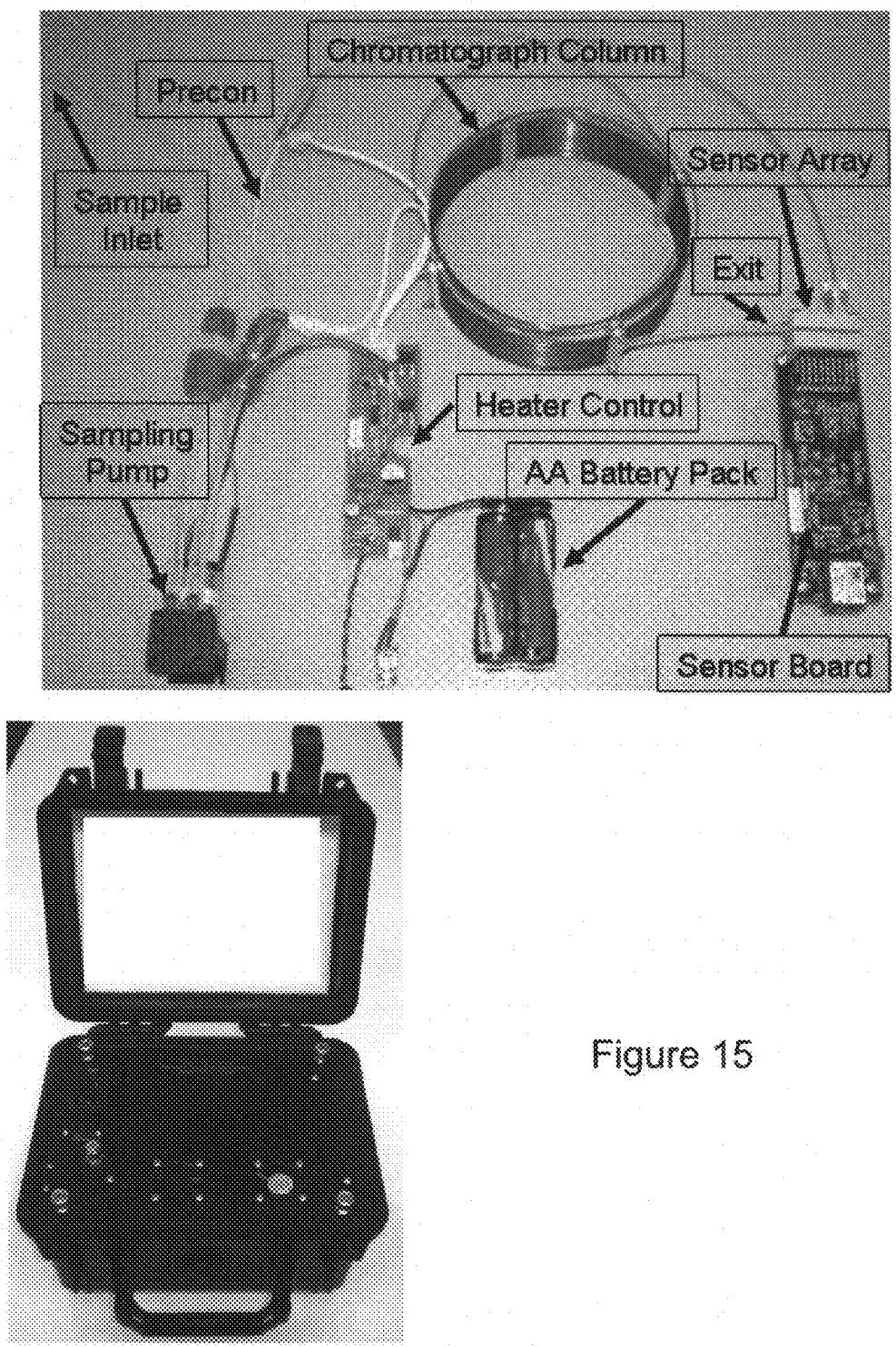
FIG. 15 shows one example of a mini-GC.

FIG. 14 is a block diagram representative of the mini-gas chromatograph (mini-GC) pictured in FIG. 15. The mini-GC comprises an inlet or vapor collector 140 through which vapor can be drawn by pump 142. In some embodiments, a liquid injector 141 may be used to mix the collected vapor with a transport medium, a reagent, a control compound or other liquid or vapor. A preconcentration stage 143 typically receives the optionally mixed or filtered collected vapor and provides an output to a chromatographic column 144. A sensor or detector 145 provides results to a controller 147 and an exhaust vapor to an exhaust component 146. The controller 147 may process the results and provide the raw and processed results to a user interface 148 for further processing and display. The detector 145 may include, for example, a MEMS chemicapacitor array (e.g. as provided by Seacoast Science of Carlsbad, Calif.). The chromatographic column 144 can include a metal capillary tube that can be directly heated, thereby eliminating the need for an oven and reducing space and power requirements and increasing speed of heating the system.

Various embodiments comprise components selected to perform specific tests or to operate under specified conditions. In one example, a system comprises a pump that can be employed to facilitate flow through the system. Heated zones can be monitored and controlled by a microprocessor. A typical vapor sampling process comprises pulling volatile chemicals onto a preconcentrator, using, for example, a pump, thermally releasing the volatile chemicals from the preconcentrator onto the head of a chromatography column, separating the volatile chemicals separate as they travel through the column and releasing speciated chemicals from the column to the detector array.

In another example, a mini-GC comprises a sampling pump 142, a pre-concentrator 143, a chromatography column 144 and a sensor array 145. The mini-GC can operate using direct injection and/or vapor sampling. The sampling pump 142 may include a flow control mechanism. The pre-concentrator 143 can be used to control collection times and temperatures. The chromatography column 144 may be configured or adapted to support programmable thermal profiles. Thermal profiles can be maintained on a heater controller and can programmed and/or configured as desired. The sensor array 145 may include a chemicapacitive sensor array. In one embodiment, a min-GC weighing less than approximately 7 lbs and having a volume of around 400 cubic inches can separate and detect chemicals and compounds in complex mixtures using MEMS Caps, MOS, IMS, SAW and other detectors without use of a carrier gas.

In certain embodiments a controller monitors and controls Mini-GC operations. The controller typically comprises a control board that can monitor a plurality of temperatures and control heaters, pumps and fans. In one example, the control board may be configured to monitor up to 4 four temperatures and control four heaters. The control board may also monitor capacitive or other sensors, filters and can condition measurement signals.

In certain embodiments, the controller may support external components such as a display (e.g. an LCD, display), relative humidity sensors, and external temperature sensor and communication devices. The use of communication devices can allow communication by wired and wireless connections including USB, Firewire, RS-232, RS-422, Ethernet, Bluetooth, Infrared, etc. The controller may communicate with one or more devices, such as a computer or other equipment using any desired protocol, including, for example, ASCII MODBUS protocol.

In certain embodiments, the controller may execute software instructions and may provide separate PID control loops for controlling temperature of the sensor array 145 and vapor injectors. PID as used herein refers to the proportional, integral and derivative terms of a closed loop feedback system including. The PID control loops can typically be configured, enabled, disabled and customized by a user.

In certain embodiments, temperature measurement may be accomplished using thermocouples, resistive temperature detectors ("RTD") and other sensors including, for example, thermal imaging. Thermocouples may include type K thermocouples and RTDs may include Pt100 RTDs. The controller can typically amplify condition and filter signals. In one example, software-based modules can normalize and linearize readings using a selected polynomial. Thermocouple can typically provide measurements up to about 320° C. while Pt100 RTDs may provide measurements up to 120° C.

Thermocouple readings may be processed by measuring cold junction temperature of the thermocouples and converting measurements to a virtual voltage of a K-type thermocouple using a reverse polynomial curve fitting. Cold junction compensation can be performed using software. An RTD can be provided a very accurate and stable electrical current and RTD wire resistance can be measured and compensated using three wire connections.

In certain embodiments, the controller can provide a plurality of pulse width modulation (PWM) outputs. A master microcontroller can monitor measurement inputs and communicate the measurements to software component located locally or on an external processor. Slave microcontrollers may receive control information from the master controller that can be used to control generation of the PWM outputs. Consequently, a master can be expanded to control more resources for accurate measurement, calculation, filtering, and communication.

In one example, PWM outputs are used to control a short heater (preconcentrator), a long heater (chromatographic column), an injector heater, a sensor ASIC heater and one or more pumps. The PWM for the ASIC heater can be filtered to a DC analog voltage and then amplified using a precision power amplifier in order to limit noise detectable at the ASIC. An ON/OFF output can be provided to control a fan for cooling certain of the heaters. For example, a fan for the long heater may be automatically turned ON when the PWM for the long heater is clear.

The short heater may uses a 12 VDC power source directly and variations in power supply can be reduced by the addition of bulk capacitors connected close to the output of the power supply. The long heater typically has a separate voltage supply that can be as high as 60 V. The pump, the fan, and the ASIC heater may use a regulated, stabilized 6V power supply to derive the 6V supply from a common 12V power supply. The injector heater can be powered by 6V, 12V or 48V.

In one example, the microcontroller defaults to a locally-controlled mode of operation for the ASIC temperature control and injector temperature control at power up. Both ASIC and injector temperature control can have separate PID constants and PID loops. Typically, other components, including certain of the heaters and the pump, may be provided with no local control mode and are remotely controlled by an external processor such as a personal computer. Typically, control parameters and constants are programmable and can be maintained by the controller in non-volatile storage such as an EEPROM.

A master microcontroller may be provided to measure and calculate temperatures at a desired rate, for example, at eight times per second. In one example, an ASIC temperature can have a sixteen level deep moving average filter which provides significantly higher resolution and accuracy, and can linearize and compensate the readings for all temperatures. The master microcontroller typically checks the mode for the ASIC heater and if it is locally controlled, the master controller may perform a corresponding PIO algorithm for the ASIC heater. The master microcontroller may immediately send a command to a slave microcontroller to set the newly calculated PWM. The master microcontroller may optionally repeat the operation for the injector heater.

In certain embodiments, the duty cycle of the PWM for the long heater may be calculated or set at 0.0%. For such a setting, the master microcontroller may send a command to the slave microcontroller to enable a fan. The microcontroller typically repeats operations cyclically to provide current, filtered data. In certain embodiments, the controller can accept broadcast and unicast ASCII MODBUS commands. Typically, a network of up to 247 devices (i.e. the MODBUS standard) can be facilitated. However, in some embodiments, a USB connection is provided which limits the number of devices in a network to potentially less than 128 devices, excluding USB hubs.

Data received from a serial port can be handled using interrupts and a special buffer can be implemented to prevent overflow or loss of data. When a complete valid message has been received, the message can be processed and a reply provided through MODBUS. There is no delay when receiving the MODBUS control function from an external personal computer or other processor. A USB to serial converter may be provided in certain embodiments.

In certain embodiments, the controller may perform measurements and communication using only power provided by a USB connection.

Figure 16:
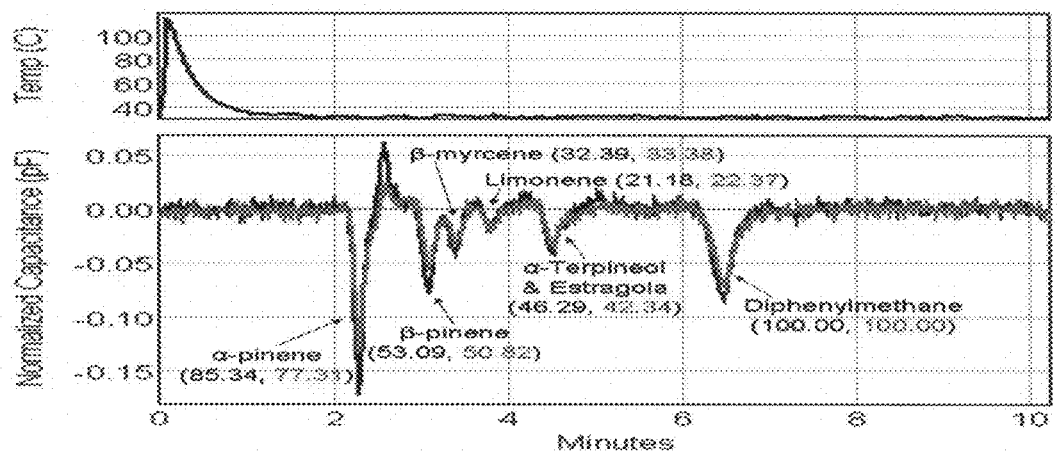
FIG. 16 is a graph showing peak integration related to preconcentrator heating.

FIG. 16 depicts results obtained using an embodiment of a mini-GC as described above. A ten-minute window is depicted and measurements of six separate chemicals on two terpene sensitive chemicapacitors are recorded. Normalized peak integration values for each sensor are indicated. The upper plot shows the heating profile of the preconcentrator including a positive peak representing humidity is observed between the $\alpha$- and $\beta$-pinene. In certain embodiments, non-polar compounds can be separated and identified including a polycyclic compound (diphenylmethane) in a mixture. For example, air from a wood drying kiln can be collected by a pump and processed by the mini-GC. Embodiments of the invention can be optimized for certain of the aforementioned analytes, and may also be amenable to low vapor pressure analytes.

Figure 17:
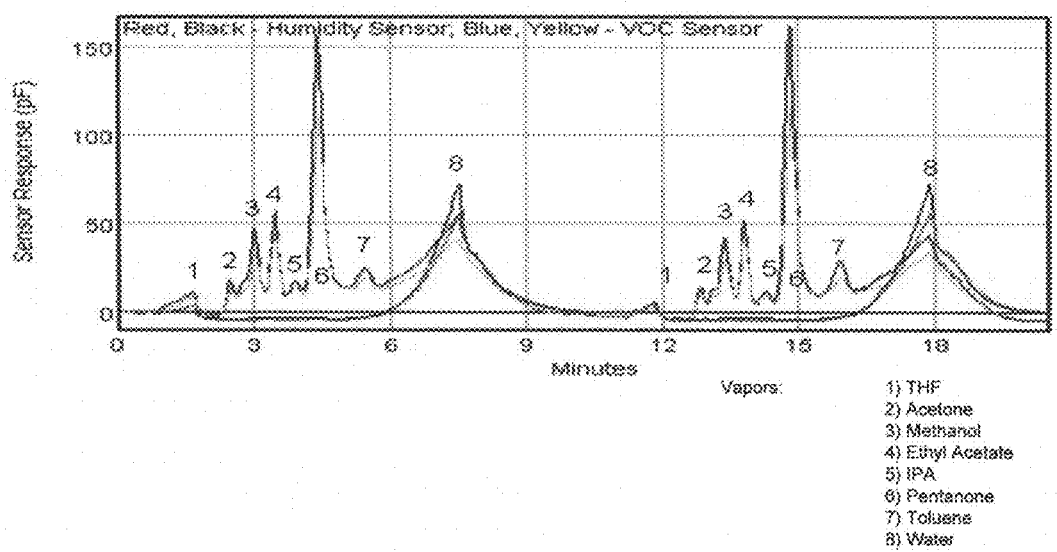
FIG. 17 is a chromatograph of gas phase sampling.
Figure 18:
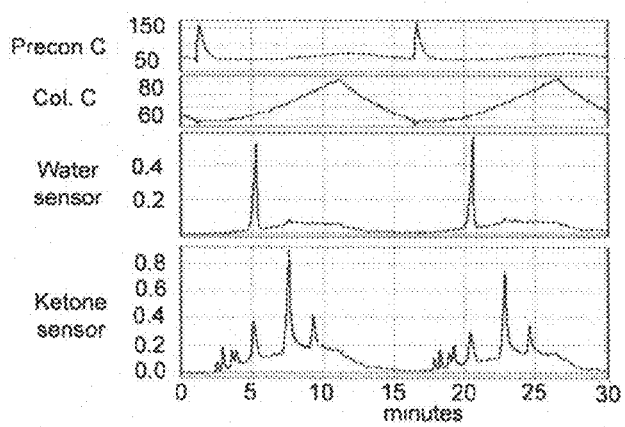
FIG. 18 includes a chromatograph of ketones obtained from a vapor flask.
Figure 18:
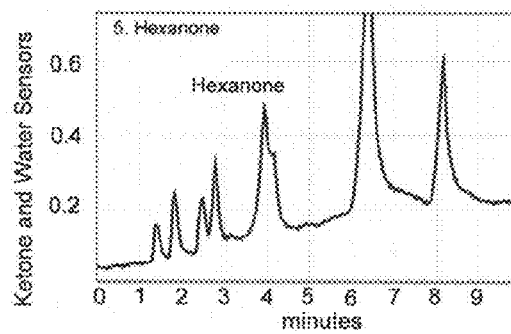
Figure 18:
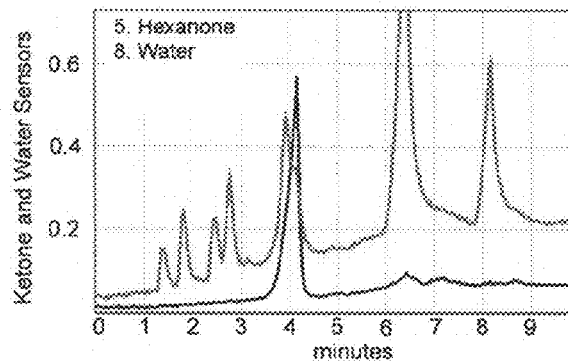

FIGS. 17 and 18 depict results obtained from embodiments comprising mini-GCs. The results were obtained by a process that included receiving a volume of air by sampling and/or direct injection, concentrating the chemical on a preconcentrator, performing chromatography to obtain separated slugs of certain of the chemicals and delivering the separated slugs to a sensor array. The process comprised certain steps that included collecting a sample onto the preconcentrator using a sample pump operated at high speed; turning off pump; heating the preconcentrator for a desired time period, such as ten seconds; operating the pump with a 15% duty cycle with continued heating for ten seconds; and turning off the heater while continuing pump operation at 15% duty cycle for several minutes. The chemicals are caused to separate and release from the column for delivery to the sensor array. FIG. 17 depicts data obtained from placing an inlet tube into a small box having seven open sample vials containing different volatile organic chemicals ("VOCs") including ethanol, methanol, ethyl acetate, isopropyl alcohol, butanol and butyl acetate. FIG. 18 depicts data obtained by injecting approximately 4 ~L of each VOC into a 500 ml flask. Vapors were collected directly from the flask.

FIG. 17 depicts a chromatograph obtained from two ten-minute cycles of gas phase sampling. Seven chemical vapors and moisture were fed to sensors such that the feed included THF, Acetone, Methanol, Ethyl Acetate, IPA, Pentanone, Toluene and Water.

Figure 19:
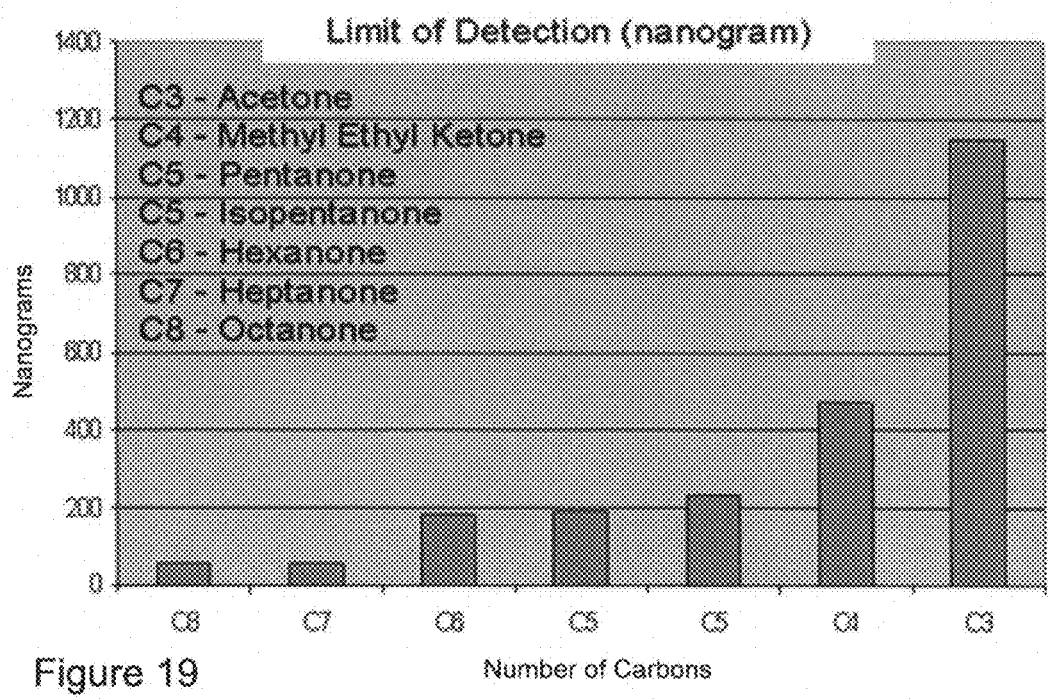
FIG. 19 charts limits of detection by molecular weight.
Figure 20:
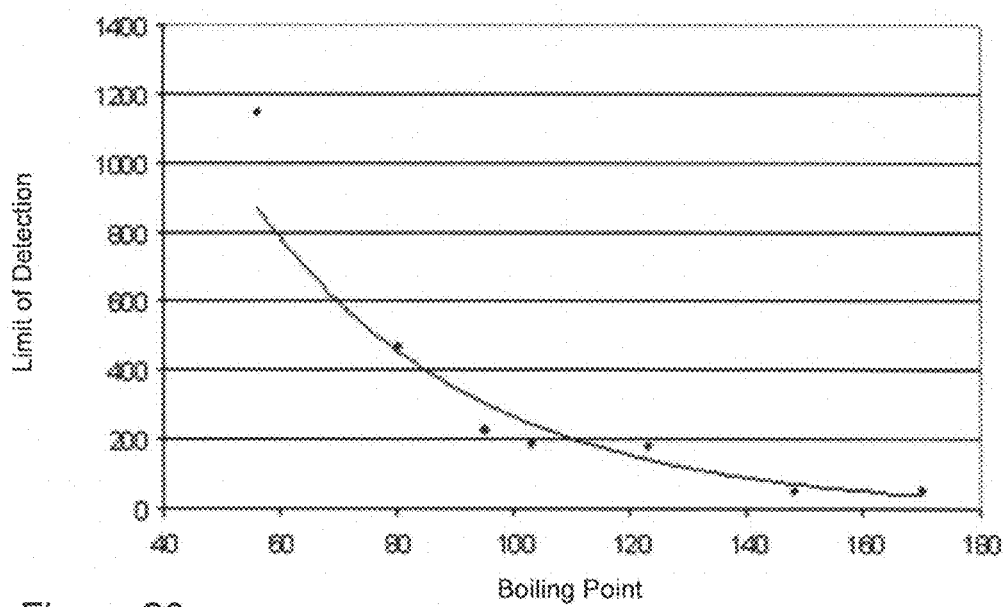
FIG. 20 depicts a graph showing detection v. boiling point trend.

In certain embodiments, general trends in the sensitivity of a mini-GC can be determined. For example, as the size of molecule in a class of compounds increases, sensitivity of the mini-GC may also increase. FIG. 19 depicts an example of such correlation using a set of ketones. In the example, sensitivity is increased for octanone (C8-50 ng) over acetone (C3-1180 ng). FIG. 20 depicts a related trend with boiling points whereby limits of detection increases with increases of the boiling point of the target chemical.

Additional Descriptions of Certain Aspects of the Invention

Apparatus and methods are described for preconcentrators and chemical sensing systems. In certain embodiments a preconcentrator comprises a hollow enclosure containing a sorbent material. In certain embodiments the enclosure comprises a capillary tube. In certain embodiments the enclosure comprises an electrically conductive or semiconductive material. In certain embodiments the material is metal. In some embodiments the metal material is stainless steel. In certain embodiments the enclosure contains a sorbent material. In some embodiments the sorbent may comprise a liquid. In some embodiments the sorbent may comprise a solid. In some embodiments the sorbent may comprise a porous ceramic material. In some embodiments the sorbent comprises a chemiselective polymer. In certain embodiments the sorbent material is coated to the inner wall of the enclosure. In certain embodiments the enclosure is configured to be heated or cooled. Some embodiments comprise resistive electrical heating. In certain embodiments the enclosure comprises a compact configuration. In some of these embodiments the compact configuration comprises a coil. In certain embodiments a preconcentrator comprises a hollow enclosure within an insulated chamber. In some embodiments the insulated chamber comprises a vacuum. In some embodiments the insulated chamber comprises an insulating material. In some embodiments the insulating material is Styrofoam. In some embodiments the insulated chamber comprises a smoothly polished interior surface. In certain embodiments a preconcentrator comprises a hollow enclosure with smoothly polished interior and/or exterior surfaces.

In certain embodiments chemical sensors comprise a preconcentrator and a chemical sensor element. In certain of these embodiments chemical sensors comprise a flow means operative to direct gas or fluid flow through the preconcentrator and to the sensor element. In certain of these embodiments chemical sensors comprise a control system operative to control sensor operation. In some embodiments the control system is operative to control heating and cooling cycles. In some embodiments the control system is operative to control gas or fluid flow. In some embodiments the control system is operative to read enclosure temperature. In certain embodiments the control system is operative to effect closed loop control of temperature cycling. In certain embodiments a chemical sensor may be electrically powered. In some embodiments electrical power may be provided by batteries.

In certain embodiments a method for making a preconcentrator comprises mounting an enclosure within a thermal chamber. In certain embodiments the enclosure comprises a capillary tube. In certain embodiments the enclosure contains a sorbent material. In some of these embodiments the sorbent material is coated to the inside of the enclosure. In some embodiments the sorbent material is physically coated onto the enclosure. In some embodiments the sorbent material is chemically coated onto the enclosure. In some embodiments sorbent materials may be thinned with a solvent, pressed into the enclosure, and dried. In some embodiments drying may comprise air drying. In some embodiments drying may comprise heat curing. In some embodiments the outside of the enclosure may be smoothly polished. In some embodiments the inside of the thermal chamber may be smoothly polished. In certain embodiments the enclosure may be compacted. In some embodiments the enclosure may be formed into a coiled shape. In some embodiments a compact enclosure may be formed by coiling a capillary tube on a mandrel tool.

In certain embodiments a method for using a preconcentrator may comprise directing fluid or vapor flow through an enclosure containing sorbent material, sorbing desired target chemicals, heating the sorbent material, and expelling desorption gases or liquids to a sensor for measurement. In some embodiments sorption and desorption may be effected with a chemiselective polymer. In some embodiments heating may be effected by thermally heating the enclosure. In some embodiments the enclosure may be heated by electrical resistive heating. In some embodiments the enclosure may be heated by thermal conduction. In some embodiments flow may be produced by pumps. In some embodiments flow may be controlled by valves. In some embodiments flow may be controlled by a control system. In some embodiments a computer may control flow and measurement operations. In certain embodiments chemical sensing may be effected by cycling measurements. In some embodiments cycling may comprise repeating a cycle of heating and cooling of the preconcentrator one or more times. In some embodiments cycling may comprise repeating one or more times one or more of the steps of directing a gas or fluid into a preconcentrator, allowing a sorbent material to adsorb target materials, heating the preconcentrator, desorbing the target from the sorbent material, directing the desorbed gas or fluid to a chemical sensing element, and measuring the target from the desorbed gas or fluid.

Although the present invention has been described with reference to specific exemplary embodiments, it will be evident to one of ordinary skill in the art that various modifications and changes may be made to these embodiments without departing from the broader spirit and scope of the invention. Accordingly, the specification and drawings are to be regarded in an illustrative rather than a restrictive sense.

What is claimed is:

1. A concentrator comprising:
    a hollow enclosure defined by a wall;
    a sorbent material coated on an inner surface of the wall that defines the hollow enclosure; and
    a heating current source providing an electrical current to the wall, wherein the hollow enclosure is heated when the electrical current passes through the wall,
    wherein the sorbent material absorbs a target chemical at a first temperature and desorbs the target chemical at a second temperature, and
    wherein the electrical current is controlled to cycle temperature within the hollow enclosure between at least the first temperature and the second temperature, thereby concentrating the target chemical in a vapor flowing through the hollow enclosure for at least a portion of the temperature cycle.

2. The concentrator of claim 1, wherein the hollow enclosure is formed from an electrically conductive material.

3. The concentrator of claim 2, wherein the electrically conductive material comprises stainless steel.

4. The concentrator of claim 2, wherein the electrically conductive material comprises a semiconductor.

5. The concentrator of claim 1, wherein the hollow enclosure comprises a capillary.

6. A method of concentrating chemicals carried in a vapor, the method comprising:
    cycling a current passing through a wall defining a hollow enclosure, wherein the wall heats the hollow enclosure when the electrical current passes through the wall;
    passing a vapor through the hollow enclosure;
    controlling the current to maintain the hollow enclosure at a first temperature for a first time period, the first temperature and first time period calculated to cause absorption of one or more target chemicals by a sorbent material provided within the hollow enclosure; and
    controlling the current to maintain the hollow enclosure at a second temperature for a second period of time, wherein the second temperature is maintained to permit desorption of the one or more target chemicals by the sorbent material, thereby concentrating the one or more target chemicals in an outflow.

7. The method of claim 6, further comprising the step of selectively cooling the capillary to regulate the temperature of the hollow enclosure between the first and second temperatures.

8. The method of claim 6, further comprising the step of detecting at least one of the one or more target chemicals in the outflow.

9. A concentrator comprising:
    a capillary formed from an electrically conductive material;
    a sorbent material coated to the inner surface of a wall that defines a hollow enclosure of the capillary; and
    a current source that provides an electrical current to the wall, wherein the wall is heated by the electrical current flowing through the wall, and wherein the electrical current is cycled to control the temperature in the capillary,
    wherein the sorbent material absorbs a target chemical at a first temperature and desorbs the target chemical at a second temperature.

10. The concentrator of claim 9, wherein the electrically conductive material comprises stainless steel.

11. The concentrator of claim 10, wherein the electrically conductive material comprises a semiconductor.

* * * * *